United States Patent [19]
Phillips

[11] Patent Number: 4,822,363
[45] Date of Patent: Apr. 18, 1989

[54] MODULAR COMPOSITE PROSTHETIC FOOT AND LEG

[76] Inventor: Van L. Phillips, P.O. Box 1873, Rancho Santa Fe, Calif. 92067

[21] Appl. No.: 29,947

[22] Filed: Mar. 26, 1987

Related U.S. Application Data

[63] Continuation-in-part of Ser. No. 761,481, Aug. 1, 1985, abandoned.

[51] Int. Cl.⁴ .................... A61F 1/00; A61F 3/00
[52] U.S. Cl. .................................. 623/27; 623/29; 623/53
[58] Field of Search .............. 623/27, 28, 32, 38, 623/50, 52, 53, 54

[56] References Cited
U.S. PATENT DOCUMENTS 693,400  2/1902  Jochinsen ......................... 623/29
4,397,048  8/1983  Brown et al. ..................... 623/27
4,547,913  10/1985  Phillips .......................... 623/27

Primary Examiner—Richard J. Apley
Assistant Examiner—Alan W. Cannon
Attorney, Agent, or Firm—Thomas P. Mahoney

[57] ABSTRACT

A prosthesis fabricated from filamentary laminates including a pylon having an upper extremity, a shin portion, an ankle portion and a forwardly extending foot portion, all integral with one another. A separate heel portion is secured directly to the foot portion and is provided in different modules of stiffness which serve, when secured to the foot portion, to greatly enhance the life-like movement of the foot and the entire prosthesis. The pylon is provided in different modules to match the weight and activity levels of a wide spectrum of individuals.

18 Claims, 6 Drawing Sheets

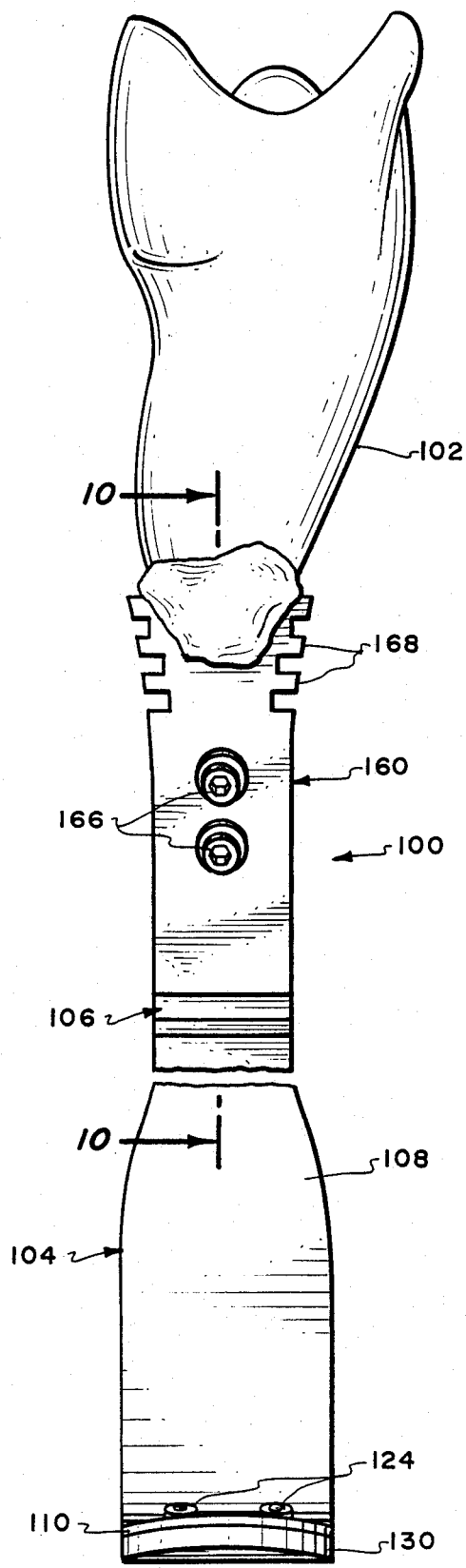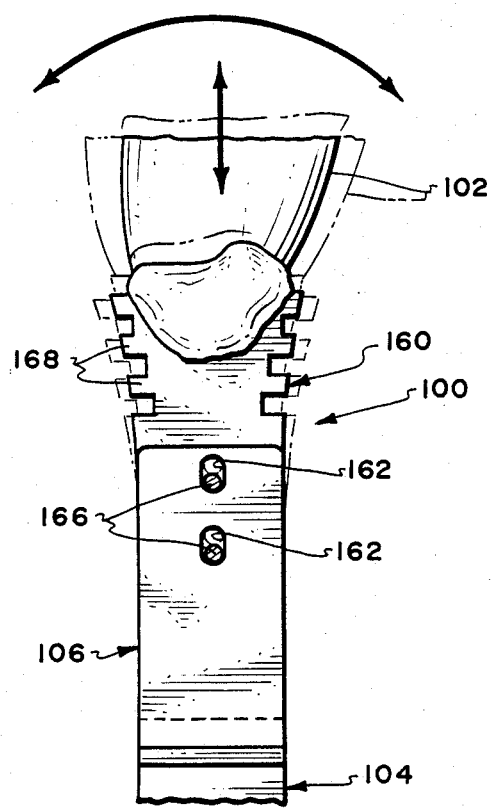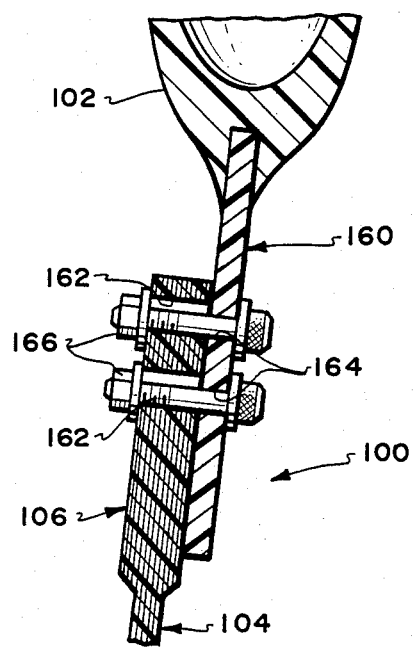
Fig. 8.
Fig. 9.
Fig. 10.

MODULAR COMPOSITE PROSTHETIC FOOT AND LEG

This application is a continuation-in-part of co-pending application Ser. No. 761,481, abandoned.

BACKGROUND OF THE INVENTION

1. Field of the Invention.

The present invention relates to prosthetic devices and, more particularly, to prosthetic foot and leg devices.

2. Prior Art.

Various types of foot and leg prosthetic devices are well known in the prior art. Such devices generally include some form of attachment for coupling the device to the dorsal end of the limb and for extending to the ground to provide body support.

Such prosthetic devices, particularly those intended to mount below the knees, are now frequently fabricated as an assembly having a leg portion and a footlike portion, with some form of pivot therebetween so as to allow the foot portion to assume various angles with the leg portion, and vice versa, as the wearer walks or goes through conventional motions. Devices of this general type are shown in U.S. Pat. Nos. 2,379,538, 3,400,408, 4,007,496, 4,089,072 and 4,161,042.

Some such prosthetic devices also include some rotatability between the foot portion and the connection to the limb, such as the ball joint of U.S. Pat. No. 3,400,408 and the swivel joint of U.S. Pat. No. 4,186,449. In general, the leg and foot portions are usually rigid members, though frequently elastic energy-absorbing members are also included to help absorb shock and for such other purposes as encouraging the ankle joint to a preferred position.

Also relevant are the teachings of my U.S. Pat. No. 4,547,913, which discloses a prosthesis characterized by the utilization of high-strength fibers and a basically unitary construction. Relevant to the continuation-in-part device are the teachings of McFarland in U.S. Pat. Nos. 1,128,018 of an articulated heel and forward portion of a foot prosthesis; Brown, 4,397,048, showing an artificial limb component fabricated from carbon fiber woven sheets; and Eyre, 4,395,783, showing the utilization of a plurality of preformed modular shin members adapted to cooperate with an identical knee support member and ankle attachment member, but differing in length of the shin tube.

Also, various methods of attachment of a prosthetic device to the end of the limb are well known, the exact manner of attachment normally depending upon exactly where the limb has been severed and the surgical technique used to close the wound. In particular, some surgical techniques result in a limb end which is particularly sensitive and, accordingly, the proper fitting of a prosthetic device to such a limb requires both careful fitting and padding.

Other techniques result in a limb end of relatively low sensitivity, allowing somewhat less of a custom fit of the prosthetic device to the limb. In any event, normally the prosthetic device is strapped to the limb to keep the prosthetic device in place throughout the wearer's normal motion, particularly when lifting the limb for walking and the like.

Because of the relatively high weight of prior art prosthetic devices in comparison to the present invention, prior art devices require tighter strapping of the device to the limb, frequently restricting the blood flow in the limb. Generally speaking, because of the weight of prior art prosthetic devices and the fact that such devices are relatively stiff and if deflectable at all, are generally deflectable in an energy-absorbing manner, the range of allowable activities of a wearer of prior art devices is generally limited to relatively slow non-strenuous activities, such as walking, etc.

More strenuous activity, such as playing tennis and other sports, running, etc., is highly limited, as the weight of the prosthetic device, the shock of the device coming down on a hard surface and the inability of the prosthetic device to return the energy absorbed therein makes the more strenuous activities with such devices either impossible or uncomfortable and awkward Although the prior art teaches, for example, in Eyre '783, the concept of utilizing modular components in conjunction with thigh and ankle attachments, so that different shin lengths of prostheses may be supplied, there is no teaching of the concept, disclosed hereinbelow, of a single modular pylon adapted to be cut to accommodate lower leg portions of different lengths without the necessity of providing different modules.

Moreover, prior leg prostheses have, with the exception of that disclosed in my previously issued patent, been characterized by undue rigidity, mechanical-like action and difficulty of fitting to the limb of the person for whom the prosthesis is intended.

BRIEF SUMMARY OF THE INVENTION

A composite prosthetic foot and leg which allows a high degree of mobility on the part of an amputee is disclosed. The prosthetic foot and leg utilizes a resin impregnated high-strength filament structure for the leg portion, the foot portion and heel portion, with all three regions being provided with substantial elastic flexibility, preferably of high-energy return characteristics so as to give the wearer high mobility with a relatively natural feel. All three portions of the prosthetic foot and leg are rigidly joined, with the flexibility of the leg portion adding to the flexibility of the foot and heel portions in response to both torques about the ankle, as well as about a vertical axis, while simultaneously providing sidewise rigidity of the structure.

Also disclosed is a prosthesis of the character of that shown in my previously issued patent which incorporates a modular shin portion, said modular shin portion being characterized by two regions, namely, a lower flexible region and an upper rigid attachment region. The lower flexible region is normally of approximately ten inches in length and the upper rigid attachment region can be of any desired length, but is so dimensioned as to permit it to be cut to accommodate the needs of a wide spectrum of leg lengths. Therefore, the necessity for providing a plurality of modules of the shin portion of the leg is dispensed and the attachment portion can be readily cut to accommodate the particular individual to whom the prosthesis is being fitted.

One of the major problems encountered in the design, manufacture and adaptation of leg prostheses to the needs of a particular individual is the large number of variables which are encountered in the adaptation of prior art prostheses to such individuals. Among the major variables are, of course, the weight, height, normal gait; and activity level of the individual being fitted with the prosthesis.

Therefore, I provide by the prosthesis of my invention adjustment and mounting means which, in addition to the modular construction of the shin portion of the prosthesis also include mounting and adjustment means adapted to facilitate the accommodation of a wide spectrum of variables encountered in the adaptation of the prosthesis to the needs of different individuals.

Therefore, while the length of the shin portion of the prosthesis can be uniform, as provided for adaptation to the height of the individual, I have provided a number of different modules of the shin portion of the prosthesis adapted to accommodate the weight and activity factors encountered in the fitting of the prosthesis to different individuals.

Moreover, in addition to the novel adjustment and mounting means for the shin portion of the prosthesis, I have provided an almost infinite variety of adjustments for the toe and heel portions of the prosthesis, thus permitting the toe and heel portions to accommodate the most subtle variations in the gait and orientation of the heel and toe portions with respect to each other.

BRIEF DESCRIPTION OF THE DRAWINGS

FIG. 8 is a front elevational view of the prosthesis taken from the line 8—8 of FIG. 7;

FIG. 9 is a fragmentary, partly sectional view taken from the broken line of 9—9 of FIG. 7;

FIG. 10 is a fragmentary, partly sectional view taken from the broken line 10—10 of FIG. 8;

DETAILED DESCRIPTION OF THE INVENTION

Figure 1:
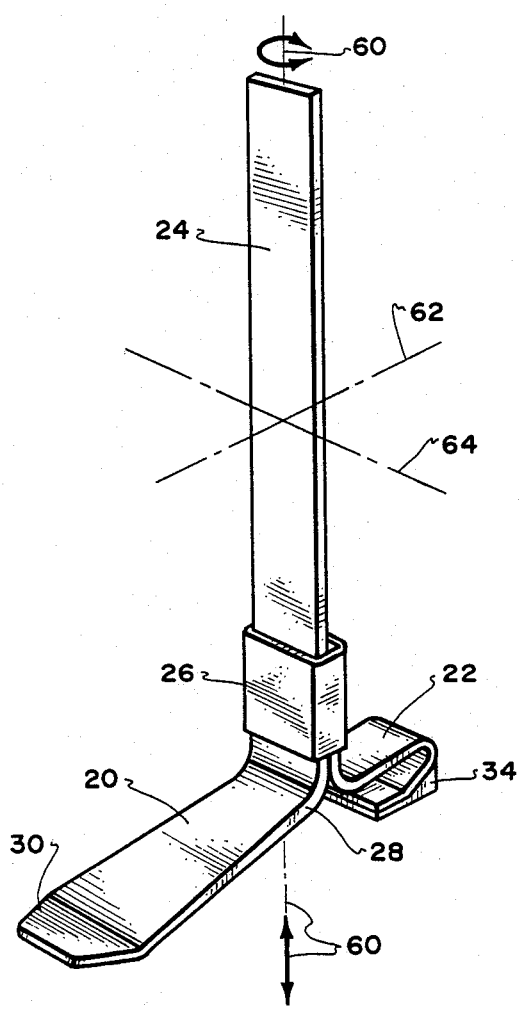
FIG. 1 i a perspective view of one embodiment of the prosthetic foot and leg in accordance with the present invention.

First referring to FIG. 1, a perspective view of one embodiment of the present invention may be seen. As is characteristic of the other embodiments of the present invention, the embodiment of FIG. 1 may be characterized as an assembly in that the foot portion 20, the heel portion 22 and the leg portion 24 are all attached to each other at the ankle region by a binding 26, as opposed to having characteristic ankle pins or pivots normally found in prior art prosthetic devices. The device of FIG. 1 is not rigid however, in that the high-strength resin impregnated filament structure of the device, coupled with the specific geometry of the individual elements, provides substantial compliances in the device with respect to certain specific types of loads, and, more particularly, non-dissipation compliances, so that the energy imparted to the device during deflection is returned by the device as the definition ceases, much like a taut muscle in combination with an ankle joint or the various foot bones and muscalature would accomplish.

In particular, both the foot portion 20 and the heel portion 22 are proportioned to serve as flat spring-like members so that the foot and heel will provide both a strong cushioning effect and energy storage in response to vertical loads on the respective portion of the prosthetic device. In particular, the spring rates of these two members are low so that the members, depending upon the exact direction of the load, will provide a very substantial non-energy absorbing compliance in the vertical direction. In that regard, it will be noted, by way of example, that the region 28 of the foot portion is thicker than the extremity 30 of the foot portion, which is desirable for a number of reasons.

Figure 2:
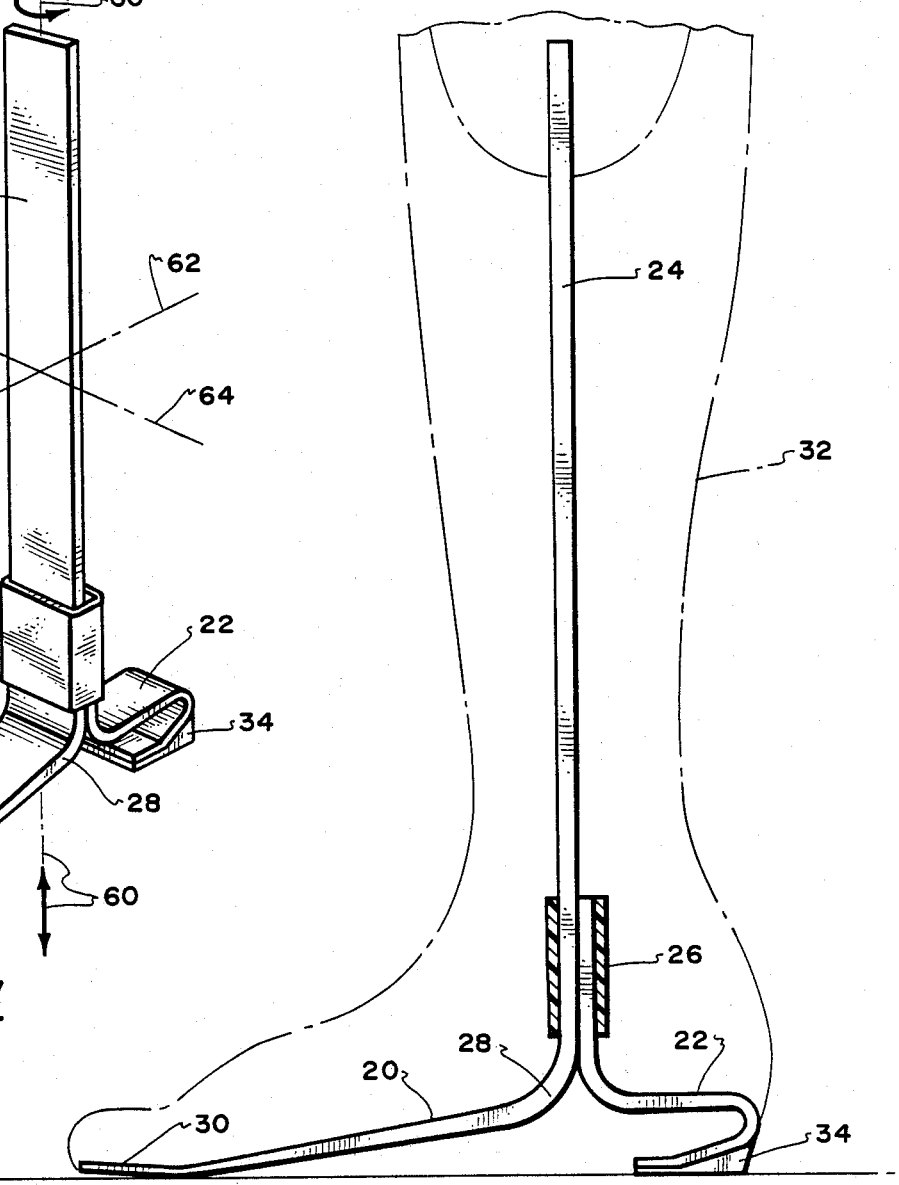
FIG. 2 is a side view of the device of FIG. 1.
Figure 3:
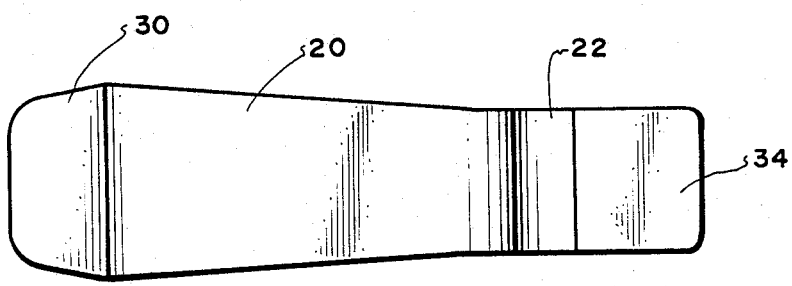
FIG. 3 is a bottom planform view of the device of FIG. 1.
Figure 4:
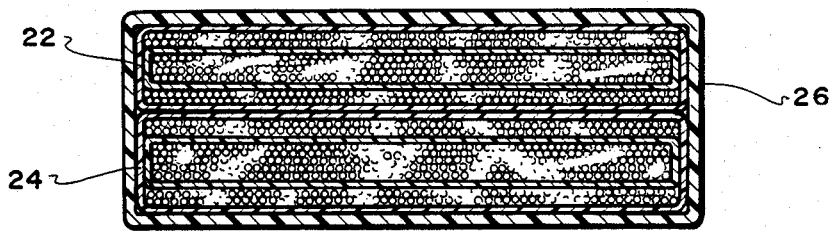
FIG. 4 is a cross section of the device of FIG. 1 taken through the ankle region thereof.

First, the planform of the foot portion 20, shown in FIG. 3 as a bottom view of the prosthetic device, more closely resembles the planform of an ordinary foot, thereby being more accommodating to a conventional shoe when worn in conjunction with a light foam rubber or other covering 32, shown in phantom in FIG. 2. In addition, however, the taper in thickness from the thicker region 28 to the thinner region 30 provides a less compliant structure in the regions of higher bending moments. This has the dual effect of reducing the maxiumum stress of the foot portion, and of much better distribution of the deflection of the foot portion throughout a major portion of the length thereof to provide greater vertical compliance of the foot portion, particularly if the wearer has that knee forward to concentrate the weight supported by that leg entirely onto the toe region.

As previously stated, the heel portion 22 is also configured to intentionally provide natural flexibility in response to vertical loads, again in a substantially non-energy absorbing manner. Since the heel support is generally much closer to the ankle region at the lower end of the leg portion 24 than is the ground contact of the foot portion 20, the heel portion 22 is purposely formed as a U-shaped structure to provide greater length in the filament-reinforced structure for increased compliance, while maintaining overall load-carrying capabilities. In the embodiment shown in FIGS. 1 and 2, an elastometric heel pad 34 is used in addition for purposes of increasing the compliance. In that regard, tests to date with prototype prosthetic devices fabricated in accordance with the present invention indicate that the compliance readily obtainable in the toe portion 30 is approximately correct, but that the heel of the device and the mobility of the user may be even somewhat further enhanced by making the heel portion 22 even more compliant. This may be achieved by making the heel portion thinner so that the spring rate of the heel portion is lower, though the compliance which may be obtained in this manner alone appears limited because of the attendant increase in stress and corresponding reduction in load-carrying capacity associated with the more compliant structure. The heel portion 22 may be made more compliant, however, by making the filament-reinforced structure thinner in the region of bending to provide greater flexing capability with some additional means being provided to share or carry the majority of the load without offsetting all of the increased compliance as a result of the thinner structure.

The preferred manner of fabrication of the prosthetic foot and leg is to use a combination of longitudinal (lengthwise) filaments in the leg, foot and heel portions interspersed with a fraction of transverse filament to bind the longitudinal filaments together and prevent separation thereof under load. A ratio of approximately 70 percent longitudinal or 90 degree filament and 30 percent transverse or 0 degree filament has been found suitable. The longitudinally oriented filaments are arranged in laminae which are located in immediate contact with one another.

Excellent results have been achieved using carbon filament with an epoxy binder. The first unit to be evaluated has a leg width of approximately two inches, a thickness of 0.3 inches, a toe length of 5.375 inches and a leg length of 12 inches (to be trimmed for fitting as required). The calculated maximum stress in the foot and heel regions for a 135-pound load is 25,286 psi in tension and compression (flexural stress) and 338 psi in sheet.

The vertical spring rate of this first unit is approximately 735 pounds per inch, giving a deflection under a 135-pound static load of almost one-fifth of an inch. Obviously, the deflection under dynamic loads, such as during walking or even more vigorous activity such as running or playing tennis, frequently is much higher. In that regard, because of the very low weight of the prosthetic foot and leg, the flexibility thereof and its ability to return energy imparted to the leg during deflection as the load thereon is decreased allows the user to participate in such sports as tennis in a very vigorous and effective manner.

While some prior art prosthetic feet and legs have achieved some degree of angular freedom at the ankle, by providing an appropriate bearing at that position, the present invention obtains the same freedom by a substantial compliance about the vertical axis 60 (see FIG. 1) as a result of the cross section and length of the leg portion 24.

In that regard, the first unit described above has a torsional spring rate about the vertical axis of approximately 14 inch pounds per degree of rotation between the top of the leg portion and the foot and heel portions. Finally, it should be noted that the configuration of the leg portion of the preferred embodiments of the present invention, particularly the relatively high area moment of inertia of the cross section of the leg portion 24 taken along a longitudinal axis 62 and the relatively low area moment of inertia of the same cross section taken along a transverse axis 64, provides a very rigid structure about the axis 62, but substantial non-energy absorbing compliance about axis 64, which imparts to the prosthetic foot and leg the rotation capabilities of an ankle joint. This compliance is, of course, limited, though is sufficient to significantly enhance the performance of the prosthesis.

A second unit has also been fabricated and tested, this unit also being fabricated using epoxy impregnated carbon filament. The second unit also has a width of two inches, but a slightly thicker leg of 0.32 inches. The second unit has a toe length of 5.75 inches, a leg length of 13 inches, a maximum stress for 135-pound load of 23,684 psi in flexing and 316 psi in sheet. The vertical spring rate of the second unit is 772 pounds per inch, with the torsional spring rate being 15.6 inch pounds per degree.

Both prototype devices have given excellent results during the testing thereof. Both are very lightwight, consuming less energy of the user, reducing loads applied to the dorsal end of the severed limb and allowing substantial reduction of the strapping tension to hold the prosthesis to the limb. This substantially aids in the comfort of the user and permits normal blood circulation in the limb. While the two embodiments fabricated to date have be fabricated using carbon filament, other filament types may also be used, such as glass, Keylar and nylon, by way of example, to insure lightweight and structural and dynamic characteristics consistent with the amputee. In that regard, the strength and stiffness of the device can be tailored to demand in each axis of freedom independently by simple dimensional and/or ratio changes, thus simulating multiple axis muscle systems in a natural ankle and foot. Also, the differences in filament types (carbon, glass, etc.) substantially affect spring rates, giving a further degree of selection and control of the characteristics of the device.

The foregoing embodiment of composite prosthetic foot and leg provides an amputee with an agility enabling many activities heretofore thought impossible. The device has a disadvantage, however, in that because it is generally fabricated as a one-piece assembly, the interchanging of the various parts to enable the assembly of a prosthesis of a size matching the size of the natural leg of the amputee is not possible. Similarly, since the flexing of the leg portion depends upon the length of the leg portion and the leg portion must have a length matching the needs of the particular amputee, custom manufacturing of the prosthetic device is generally required to adequately satisfy the characteristics and requirements of each amputee. The improvement of the embodiment of FIGS. 5 and 6, however, generally solves this problem, allowing the fabrication and stocking of certain limited standard parts which then may be fitted to any of most amputees and still achieve all of the desired characteristics of the device.

In particular, the distance from the end of an average amputee's stump to the floor is approximately 13 inches, with 98 percent of the amputees ranging between 10 inches and 17 inches. This, in turn, means that if the upper extremity of the shin portion of the prosthetic foot and leg of the present invention could be trimmed during fitting without affecting the elastic properties thereof, the parts for the prosthetic devices could be manufactured as standard components and selected, cut and fitted as required from the stock parts.

This, in turn, is achievable by not making the leg portion of substantially uniform cross section as shown in the embodiment of FIGS. 1 through 4, but rather by fabricating the foot and leg portion to have the desired flexibility and spring characteristics contained in the portions thereof below an elevation of approximately 10 inches, with the extremity thereabove being much stiffer and preferably of generally uniform cross section so as to allow convenient attachment thereto regardless of the elevation at which such extremity is cut.

Obviously, the desired rigidity of the upper extremity can be achieved by increasing both the width and thickness of the section in that region, though the spring rate about a vertical axis and about a transverse horizontal axis are both more dependent upon the thickness thereof and, accordingly, the desired rigidity may be achieved primarily by thickening the extremity independent of whether the extremity is also widened.

Figure 5:
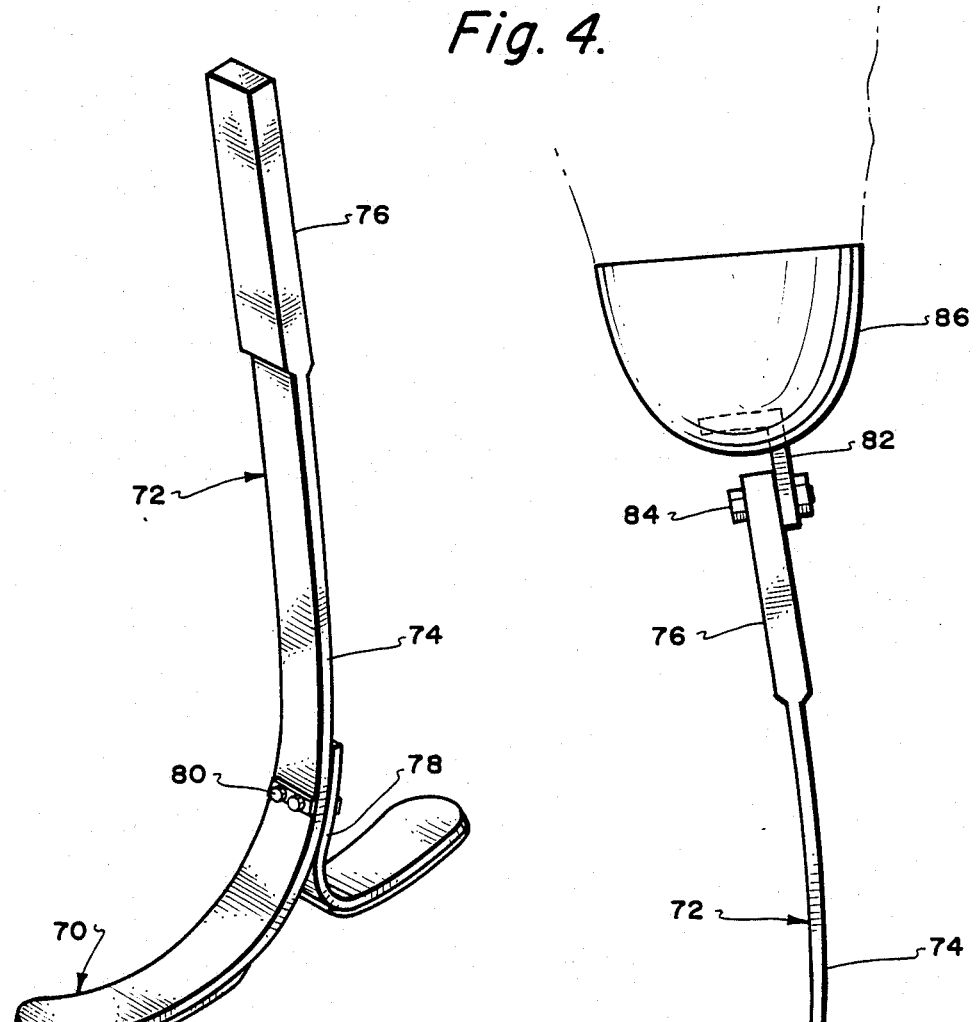
FIG. 5 is a perspective view of a prosthesis manufactured in accordance with the teachings of my invention which incorporates a shin portion whose length is adaptable to the height of a wide variety of individuals.
Figure 6:
FIG. 6 is a side elevational view of the prosthesis shown in FIG. 5 illustrating the assembly thereof and modification to accommodate the height of the amputee being fitted with the prosthesis.

Now referring to FIGS. 5 and 6, a filament reinforced foot and leg having the above-described characteristics is shown. In this embodiment, the foot portion, generally indicated by the numeral 70, and the shin portion, generally indicated by the numeral 72, are fabricated as an integral filament reinforcing structure, with both the foot 70 and the shin portion 74 of the leg being proportioned to have the desired flexibility and spring characteristics about both the vertical torsional axis, and about a horizontal transverse axis in response to a user standing on the forward part of the foot portion 70.

The upper extremity 76, on the other hand, is substantially thicker than the foot portion 70 and the flexible shin portion 74 of the leg, thereby making the upper extremity 76 substantially rigid. The extremity may also be made wider than the flexible shin portion 74, if desired, for ease of attachment, as shall be subsequently described, though the rigidity is achieved primarily by the additional thickness rather than width.

Also, preferably the upper extremity 76 is of generally rectangular section, straight and uniform in cross section throughout its length so that said upper extremity of the prosthetic foot and leg will have a known size and section n of where that extremity is cut during fitting. In general, the rigid upper extremity 76 should extend to approximately 10 inches from the floor level, or stated otherwise, the flexible shin portion 74 preferably extends upward to a level not exceeding 10 inches from the floor to allow the cutting of the rigid upper extremity 76 as required to accommodate the needs of nearly all amputees, while still leaving a sufficient length of the rigid upper extremity 76 for the attachment of the stump fitting.

Also, in the embodiment shown in FIG. 5, it will be noted that the heel member 78 is not integrally bonded to the foot and leg member, but rather is fastened thereto by bolts 80. It has been found that by using appropriate backup plates under the heads and nuts of the bolts and, of course, an adequate provision for locking the nuts onto the bolts, the two parts may be bolted together with sufficient rigidity so as to retain the parts as desired without interfering with the desired flexibility of the part. In that regard, use of the detachable heel provides further flexibility in the manufacturing and the mating of the various parts to the requirements of any particular amputee.

The preferred attachment of the prosthetic foot and leg of this embodiment is illustrated in FIG. 5. In particular, the rigid upper extremity 76, once cut to length, bolts to an attachment bar 82 by bolts 84, the attachment bar 82 being captured within a filament reinforced socket structure 86 formed by laminating and curing a resin impregnated high-strength filament cloth. This is to be distinguished from attachments wherein the leg section itself is embedded in a laminated socket structure in a permanent manner so that none of the parts may be replaced if worn or damaged for some reason. Thus, in this improved embodiment, the prosthetic foot and leg or parts thereof may be retained and the socket be discarded.

Referring to the drawings, and particularly to FIGS. 7-16 thereof, I show a prosthesis 100 which constitutes a major improvement over the previously disclosed embodiments of my invention. The prosthesis 100 is a lower leg prosthesis, that is, a prosthesis particularly adapted for utilization by amputees whose lower leg has been severed in such a manner that a residual stump below the knee remains which may be received in a stump socket 102 to permit the securement of the prosthesis 100 to said stump by a variety of well-known expedients.

The prosthesis 100, as best shown in FIGS. 7-10 of the drawings, includes a generally vertically oriented pylon 104 which is fabricated from resin-impregnated filamentary materials. Typical of such materials utilized are carbon fiber filaments impregnated with epoxy resins. It is desirable that the length of the filaments be such that they extend from the upper extremity 106 of the pylon 104 through the shin portion 108 of said pylon and into the forwardly extending foot portion 110 thereof. When impregnated with epoxy or other suitable resins, the elongated fibrous or filamentary materials establish a continuum which provides the previously mentioned minimal energy absorption compliance, thus providing to the pylon the inherent resilience and lifelike movement which imparts to the prosthesis the natural movement closely simulating the flexure and gait of a normal limb.

In discussing the integrated areas of the pylon 104 it is convenient to consider the lower arcuate extremity of the pylon intermediate the shin portion 108 and forwardly extending foot portion 110 as an ankle portion 112.

The upper extremity 106 of the pylon 104 is of such thickness, as best shown in FIGS. 7, 10 and 14-15 of the drawings, as to rigidify said upper extremity, thus creating, substantially, a line of demarcation 114 between the compliant, resilient shin portion 108 and the upper extremity 106.

Generally speaking, as indicated in the description of the embodiment of FIGS. 5 and 6 of the drawings, the vertical length of the pylon below the thickened, rigid upper extremity 106 is approximately ten inches, and the adjustment in the length of the pylon is accomplished by providing or imparting sufficient length to the upper extremity 106 to permit the upper extremity to be cut to a desired length to achieve the overall length of the pylon.

Consequently, as previously indicated, one length of pylon 104 can be utilized to accommodate individuals of different heights or different lengths of lower leg without the necessity for providing individual length pylons.

Moreover, the rigidity imparted to the upper extremity 106 of the pylon 104 greatly facilitates the fastening of the pylon 104 in operative relationship with the stump socket 102 by various fastening or mounting means, in manners to be described in greater detail hereinbelow.

Although I have disclosed the achievement of rigidity of the upper extremity 106 of the pylon 104 by the thickening of the upper extremity 106 in fore and aft directions, it will be apparent to those skilled in the art that the rigidification of said upper extremity 106 can be accomplished by alternative means, such as the incorporation of a rigid metallic element for the rigidification of said upper extremity or by expanding the width of said upper extremity rather than thickening the same.

It will be noted that the pylon gradually tapers in thickness through the ankle portion 112 and terminates in the forwardly extending foot portion 110. To complete the foot of the prosthesis 100, a rearwardly extending foot portion 120 is provided, said foot portion having a slightly arcuate forward extremity 122 adapted to conform to the under surface of the forwardly extending foot portion 110 and being demountably secured thereto by a plurality of fasteners 124, consisting of a pair of bolt and nut washer combinations. Therefore, the heel portion 120 of the prosthesis 100 is demountably secured to the underside of the forwardly extending foot portion 110 to facilitate the securement of interchangeable heel heights or lengths of heel portions 120 in operative relationship with the forwardly extending foot portion 110.

Figure 11:
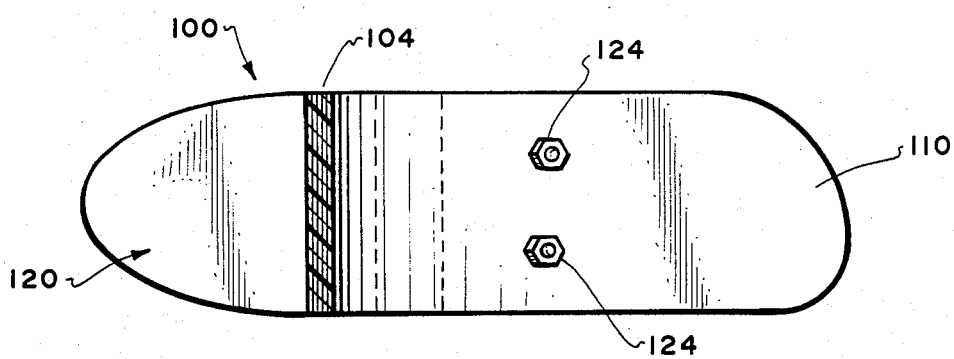
FIG. 11 is a top plan, partially sectional view, taken from the broken line 11—11 of FIG. 8.
Figure 13:
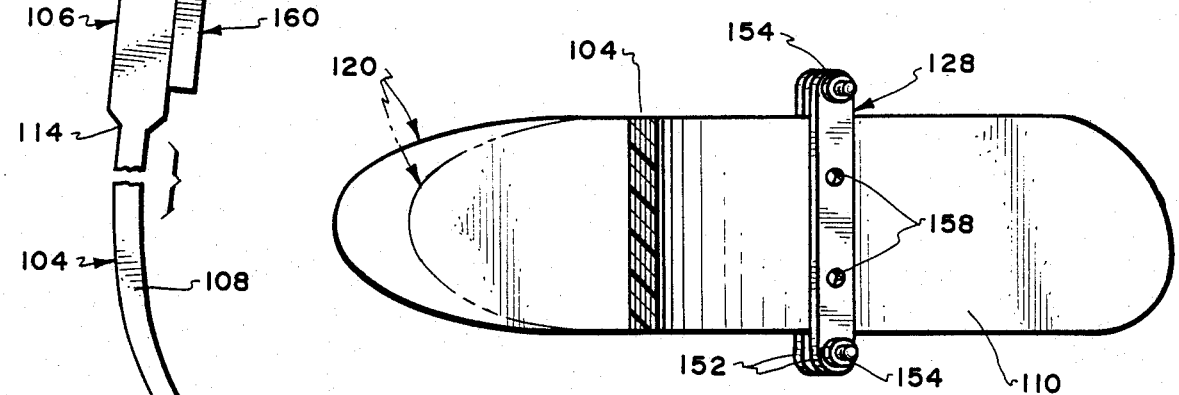
FIG. 13 is a view taken from the broken line 13—13 of FIG. 12 illustrating the fitting of a selected heel portion to the forward foot portion of the prosthesis.

It should be noted that, as best shown in FIGS. 11 and 13 of the drawings, the forwardly extending foot portion 110 of the prosthesis 100 is contoured and sized to conform to the requirements of the individual amputee.

The feasibility of providing different lengths of heel portions 120 is illustrated in FIG. 13 of the drawings, wherein the utilization of a heel portion mounting jig 128 is illustrated, the installation and operation of said mounting jig to be described in greater detail hereinbelow.

Adhesively secured to the underside of the forward extremity of the forwardly extending foot portion 110 is a resilient pad or cushion 130 and a similar pad 132 is adhesively secured to the underside of the rearward extremity of the heel portion 120. The heights and the lengths of these pads can be tailored to suit the needs of the particular individual for whom the prosthesis is intended.

For instance, the heel height can be provided in ⅜-inch and two-inch modules and the height of heel can be correlated with the predetermined nylon tilt adjustment. Consequently, the provision of various lengths of heel portions 120 coupled with the variations in the heights of the heel cushions 132 imparts a modular characteristic to the heel portion 120 of the prosthesis 100, not achievable by prior art constructions.

Figure 7:
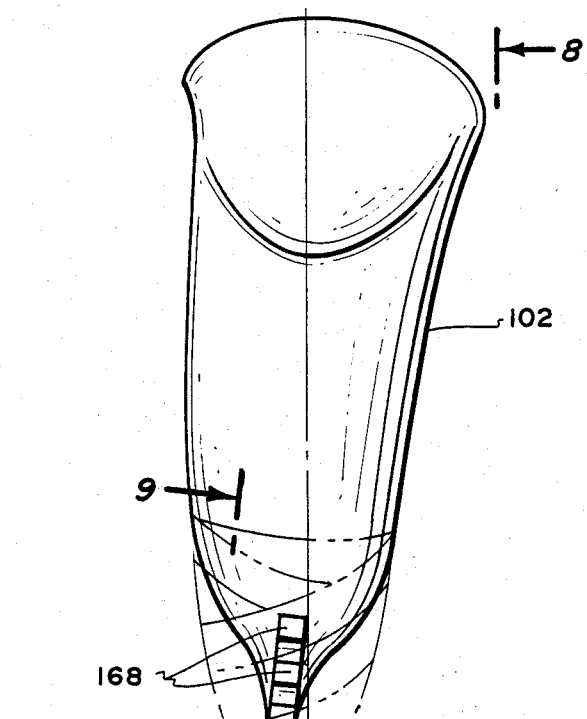
FIG. 7 is a side elevational view of yet another alternative embodiment of the invention.
Figure 15:
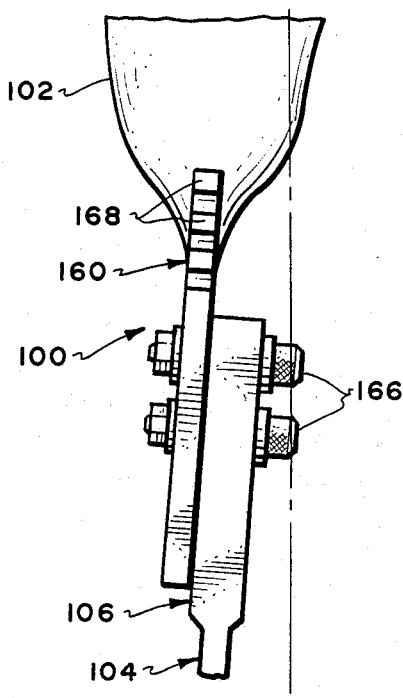
FIG. 15 is a fragmentary, side elevational view showing an alternative adjustment of the shin portion of the prosthesis.
Figure 16:
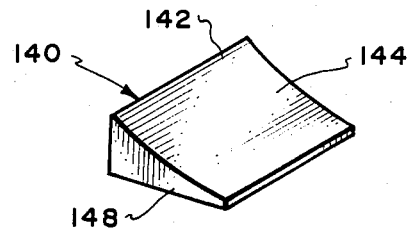
FIG. 16 is a perspective view showing a resilient wedge 16 interposable between the heel portion and forward foot portion of the prosthesis.

Contributing significantly to the adaptability of the heel portion 120 to the needs of the individual to whom the prosthesis 100 is fitted is the provision of leverage blocks 140, as best shown in FIGS. 7 and 16 of the drawings, said leverage blocks being constituted by heel wedges 142 having a curvilinear upper surface 144 conformable to the underside of the forwardly extending foot portion 110 at the intersection 146 between the heel portion 120 and the forwardly extending foot portion 110 of the prosthesis. The underside 148 of the heel wedges is relatively flat to conform to the upper surface of the rearwardly extending foot portion 120.

The heel wedges 142 are fabricated from urethane rubber and are inserted in the intersection space between the underside of the forwardly extending foot portion 110 and the upper surface of the heel portion 120, being retained in operative relationship with said surfaces by any one of a number of adhesives. The heel wedges 142 are provided in different lengths and thicknesses and, thus, determine the length of the lever arm of the rearwardly extending heel portion 120 and the consequent stiffness of said heel portion of the prosthesis.

As previously mentioned, the foot size and configuration is determined prior to the shipment of the prosthesis from the manufacturer, as are also the left and right profiles of the foot of the wearer of the prosthesis.

In addition, five different heel modules providing different degrees of stiffness are offered, and two different profiles of the heel portion 120 are provided to accommodate relatively flat-heeled shoes and relatively higher-heeled shoes. Thus, the heel height can vary from zero inches to two inches.

Figure 12:
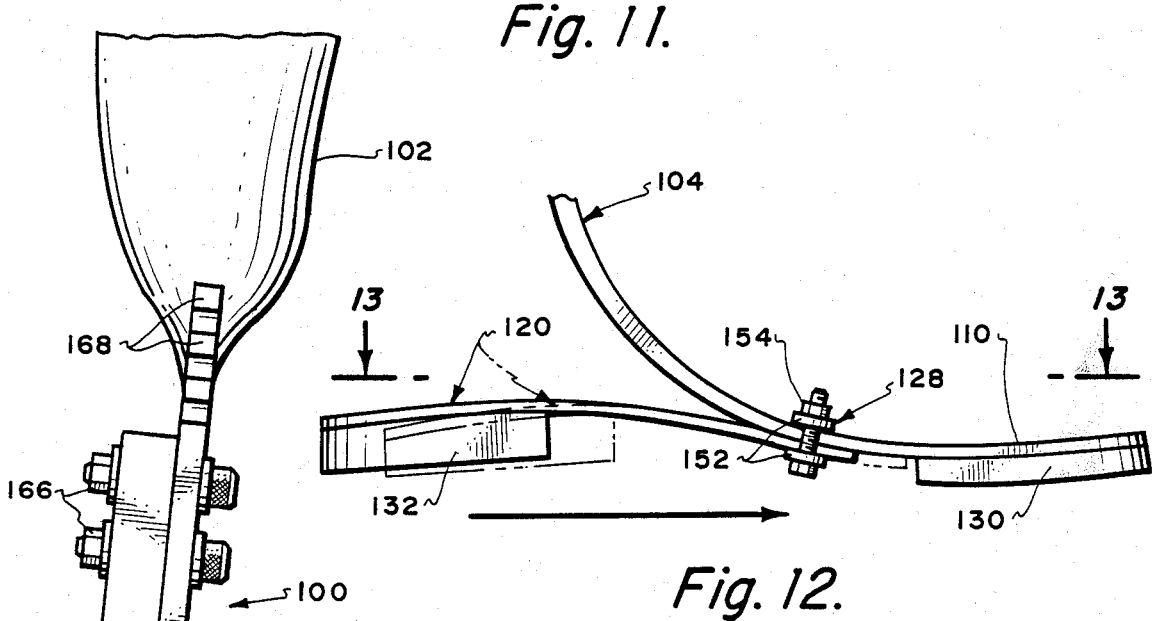
FIG. 12 is a fragmentary, side elevational view showing alternative heel lengths and adjustments utilizable in conjunction with the prosthesis of the invention.

As previously mentioned, the location of the forward extremity of the heel portion 120 with respect to the forwardly extending foot portion 110 of the prosthesis is determined by the utilization of a drill jig 128, which consists of spaced retaining bars 152 adapted to be retained in clamping relationship with the assembled forwardly extending foot portion 110 and rearwardly extending heel portion 120, as best illustrated in FIGS. 12 and 13 of the drawings. The clamping bars 152 are maintained in clamping and operative relationship with the assembled foot and heel portions 110 and 120, respectively, by means of bolt, nut and washer assemblies 154 which are tightened to insure that the selected position of the heel portion 120 with respect to the forwardly extending foot portion 110 can be maintained during the formation of corresponding holes 156 in said foot and heel portions, as best shown in FIG. 7 of the drawings.

The formation of the holes 156 is accomplished by the use of drill guides 158 in the clamping fixture 128 and the accurate adjustment of heel portion 120 with foot portion 110 may thus be accomplished.

It will be obvious to those skilled in the art that the clamping fixture 128 is utilized during the fitting process to permit the maxiumum and optimum adjustment of the heel portion 120 with respect to the foot portion 110 while the entire prosthesis is being adjusted to the specific needs of the wearer of the prosthesis. After what appears to be the optimum adjustment, the clamp is thoroughly tightened by the use of the bolt and nut combinations 154 and the drilling process by the use of the drill guides 158 is then accomplished.

Subsequently, the bolt and nut combinations 124 are inserted in the corresponding openings 156 in the foot and heel portions 110 and 120, respectively, to securely clamp the heel portion 120 in optimum physical relationship with the foot portion 110.

Figure 14:
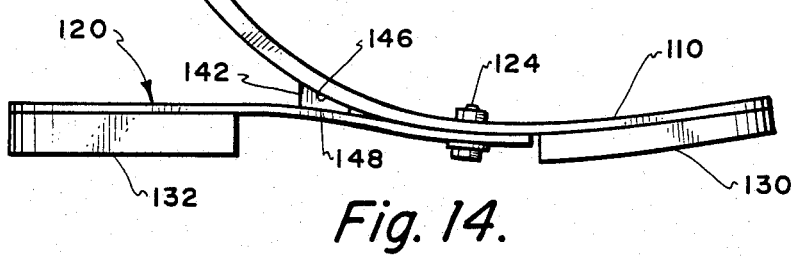
FIG. 14 is a side elevational view of the prosthesis illustrating the location of a resilient wedge between the heel portion and forward foot portion of the prosthesis.
Figure 17:
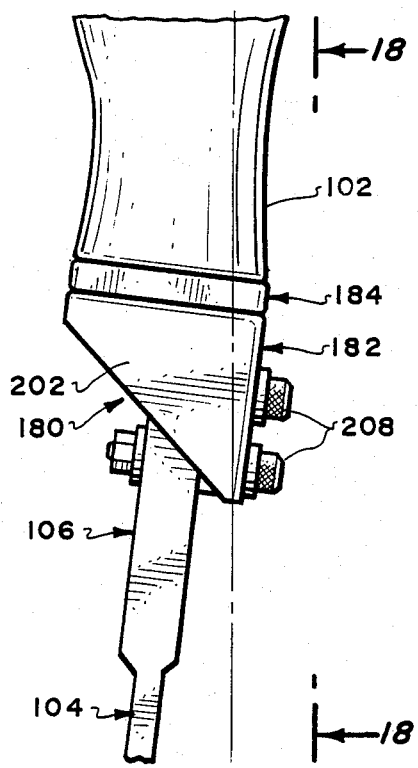
FIG. 17 is a fragmentary, side elevational view illustrating an alternative adjustable mounting means of the invention.
Figure 18:
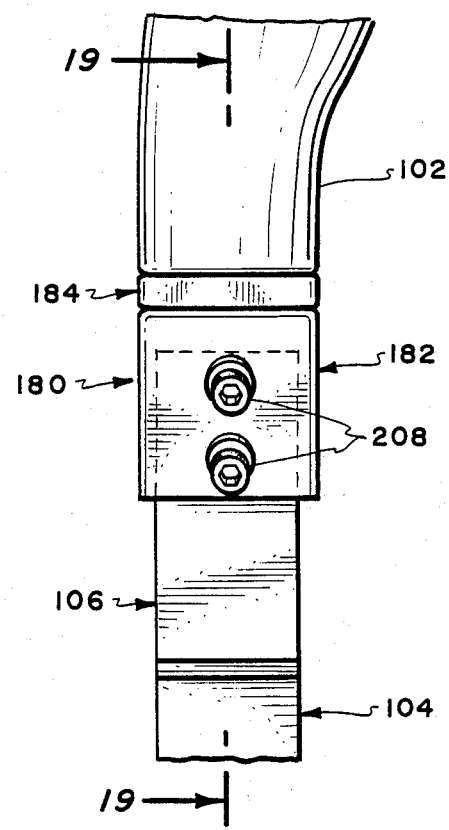
FIG. 18 is a view taken from the broken line 18—18 of FIG. 17.

To be noted is the fact that corresponding FIGS. 7 and 14 of the drawings illustrate the utilization of different heights of heel wedges 142 to adjust the lever arm of the respective heel portion 120, and, as explained hereinbelow, the low energy-abrsorbing compliance of said heel portion.

In order to provide the ultimate in accommodation of the anatomical and activity specifics of different individuals, five pylons are provided to accommodate persons weighing from 100 to 225 pounds in 25-pound increments. The number of laminae for the 100-pound person pylon is approximately 40 for a total thickness of 0.210 inches, and the number of laminae for the 225-pound person pylon is approximately 70 and a thickness of 0.340 inches. Consequently, the thickness of the shin portion 108 and, correspondingly, ankle portion 112 and foot portion 110 of the pylon 104 of the prosthesis increases as the weight or activity level of the intended user increases.

For instance, if a person weighing 200 pounds is extremely active by virtue of engaging in various sports, he will be fitted with the 225-pound pylon 104 rather than the 200-pound pylon.

In addition, the width of the pylon is adjusted to provide that the 100/125 pound and 125/150 pound pylons will be of lesser width than the three pylons accommodating individuals whose weight is encompassed in the 150-pound to 225-pound range. The two lesser width pylons are approximately 1¾ inches in width in the shank portion and 2.4 inches in the foot portion. The greater width of the three heavier weight-sustaining pylons is 2 inches in the shank portion and 2.8 inches in the foot portion.

Generally, speaking, the five pylons will be allotted to the following weight spans:
No. 1—100/125
No. 2—125/150
No. 3—150/175
No. 4—175/200
No. 5—200/225

Obviously, additional laminae are added to maintain strength as the width of the pylon is reduced. There are normally 70 plies of graphite filaments of a thickness of 0.005 inches each to achieve a total thickness of 0.350 inches for the pylon. Each of the five pylons provided for the different weight categories set forth hereinabove is approximately 0.025 to 0.030 inches greater in thickness than the lower numbered pylon.

The entire prosthesis is fabricated from carbon fiber or graphite laminates and the lay-up pattern of the laminates is characterized by longitudinal orientation of the central portion of the pylon and angular orientation at the edges of the pylon. This orientation extends from the upper extremity 106 of the pylon through the foot portion 110, thus achieving a dynamic continuity of construction and also permitting the energy-conserving compliance referred to in detail hereinabove.

In addition, there is, as previously indicated, a gradual reduction in the thickness of the pylon in the various dynamic areas thereof. For instance, in a selected pylon, the shin portion 108 will be characterized by being, 0.280 inches in thickness, the ankle portion 112 0.250 inches and the forwardly extending foot portion 110 being, coincidentally, 0.110 inches.

One of the most important aspects of the presently discussed improvement lies in the fact that the largest strain area of the foot and heel assembly has been developed to improve durability and compliance of the heel and foot portions. The direct attachment of the foot portion 120 to the heel portion 110 provides a smoother transition from heel strike through mid-stance to toe-off. In addition, the intersectional space 146 is created, permitting the utilization of the lever arm wedges 142 to provide even greater control of compliance and flexibility of the foot and heel portions 110 and 120.

A cosmetic cover may be provided for the prosthesis 100 which is preferably fabricated from tear-resistant ethylvinyl acetate foam. One desirable method of utilizing the foam is in the form of precut sheets which can be easily applied and shaped to the prosthesis 100 to accomplish the matching of the sound side of the person being fitted with the prosthesis 100.

Because of the fact that the prosthesis 100 is characterized by modularity in length of the pylon 104, heel and forwardly extending foot portion adjustment and lever arm adjustment of the heel portion 120, the achievement of the tuning to attain the nuances of precise movement and accommodation of which the prosthesis 100 is capable becomes a function of the connection or mounting of the prosthesis 100 in operative relationship with the stump socket 102.

For instance, the pylon 104, through the intermediary of the rigid upper extremity 106 thereof, may be secured in operative relationship with stump socket 102 by the utilization of commercially available modes of connection and mounting, such as the mounting link disclosed in U.S. Pat. No. 3,659,294. Such an adjustable link can be modified to accommodate the upper extremity 106 of the pylon 104.

However, I have developed several mounting and connector expedients exemplified, in one instance, by the pylon connector or mounting 160, FIGS. 7-10 of the drawings.

In order to cooperate with the pylon connector mounting 160, the upper extremity 106 of the pylon 104 is provided with elongated slots 162 corresponding to bores 164 provided in the mounting connector 160, as best shown in FIG. 10 of the drawings. The upper extremity 106 has bolt, washer and nut combinations 166 inserted through said openings and slots, 164 and 162. Therefore, said upper extremity of said pylon can be adjusted upwardly and downwardly with respect to the connector mounting 160, as graphically illustrated in FIG. 9 of the drawings.

The upper extremity of the mounting connector 160 incorporates a plurality of dentate projections 168 which may be embedded in epoxy or other resin after the adjustment of the prosthesis 100 with respect to the stump socket 102.

Various adjustment means can be utilized in adjusting the prosthesis 100 with respect to the stump socket prior to the permanent affixation of the prosthesis 100 to the stump socket 102, but it is desirable to utilize an alignment tool, not disclosed, which facilitates the alignment process to achieve the various alignment alternatives of medial/lateral; interior/posterior; toe-in/toe-out; flexion/extension; and inversion/eversion adjustments.

Once the desired adjustment of the prosthesis 100 has been achieved, the cosmesis covering previously referred to can be applied to the prosthesis 100 to impart a cosmetic appearance to the said prosthesis.

It will be noted that the upper extremity 106 of the pylon 104 can be directly connected to either the anterior or posterior faces of the lower extremity of the connector mounting 160 to achieve the desired orientation of the pylon 104 in operative relationship with the stump socket 102. Moreover, various types of shim blocks similar to the block 172 shown in FIG. 21 of the drawings can be interposed between the corresponding surfaces of the connector mounting 160 and the upper extremity 106 of the pylon 104 to achieve a greater range of adjustment than possible by mere affixation of said upper extremity to said connector mounting.

Figure 21:
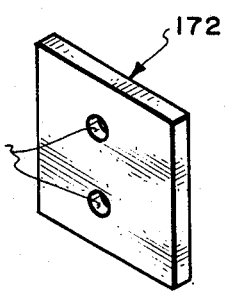
FIG. 21 is a perspective view of the vertical shin plate utilized in conjunction with the aforesaid mounting bracket.
Figure 22:
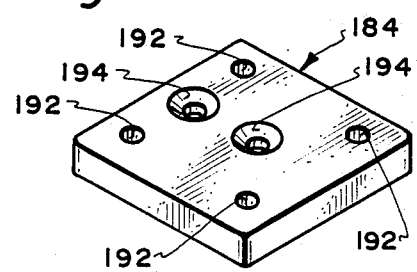
FIG. 22 is a perspective view of the horizontal shin plate utilized in conjunction with said mounting bracket.

The block 172, illustrated in FIG. 21 of the drawings, is co-planar and square. Various alternative forms of blocks, including wedge-shaped angular blocks, can be provided in substitution for the block 172 to accomplish, not only anterior or posterior adjustment, but angularity thereof.

Another mounting connector 180 is illustrated in FIGS. 17–20 and 22 of the drawings and consists of a right-angularly formed bracket 182 coacting with a mounting plate 184. The mounting plate 184 is secured in operative relationship with the lower extremity of the stump socket 102 by means of fasteners 186, FIG. 19, and incorporates a pair of fasteners 188 adapted to secure the bracket 182 in proper adjustment with the stump socket 102.

Figure 19:
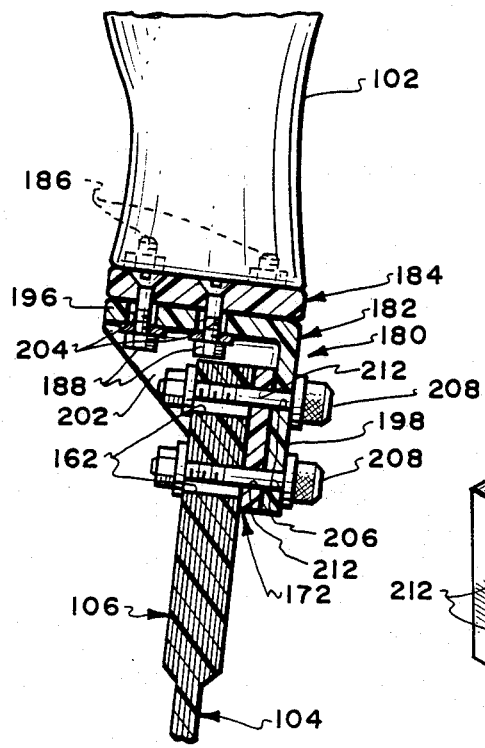
FIG. 19 is a vertical, partially sectional view taken from the broken line 19—19 of FIG. 18.
Figure 20:
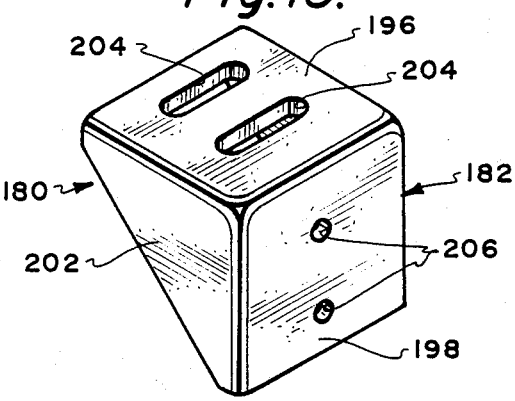
FIG. 20 is a perspective view of the adjustable mounting bracket of FIG. 17.

The mounting plate 184 incorporates a plurality of mounting openings 192 for the reception of the mounting fasteners 186 and a pair of centrally-located adjustment openings 194, said adjustment openings receiving the adjustment and mounting fasteners 188, as best shown in FIG. 19 of the drawings.

The mounting bracket 182 provides a horizontally-oriented leg 196 and a vertically-oriented leg 198 whose rigidity is enhanced by angular gusset plates 202.

Elongated adjustment slots 204 are provided in the horizontal leg 196 and securement openings 206 are provided in the vertical leg 198. The fasteners 188 of the mounting plate project through the adjustment slots 204 of the horizontal leg 196, and the accomplishment of various modes of adjustment is predicated upon the fact that, not only are the adjustment slots 204 provided for cooperation with the adjustment fasteners 188 on the mounting plate 184, but the width of the slots, as best shown in FIG. 19 of the drawings, is somewhat wider than the diameter of the bolts constituting a part of the adjustment fasteners 188 of the mounting plate 184, thus permitting, not only the lateral adjustment of the prosthesis, but angular adjustment as well with respect to the mounting plate 184.

Moreover, the adjustment block 172 may be interposed between the corresponding surfaces of the vertical leg 198 and the upper extremity 106 of the pylon 104 to achieve greater flexibility of adjustment, said adjustment block 172 being secured in operative relationship with the vertical leg and upper extremity 182 and 106, respectively, by means of bolt, nut and washer fastener combinations 208 extending through openings 212 which register with corresponding openings or slots 162 in the upper extremity 106 of the pylon 104, as previously discussed in the showing of FIG. 10 of the drawings.

As discussed hereinabove, the shape of the shim blocks 172 can be modified by imparting angular surfaces thereto to achieve angular adjustment of the pylon 104 with respect to the mounting connector 180. It will be obvious to those skilled in the art that the mounting connector 180, in addition to its basic rigidity and strength, provides a flexibility of adjustment which harmonizes with the modular nuances of compliance achieved by the previously discussed elements of construction of the prosthesis 100.

Consequently, the light weight, strength and resilience of the prosthesis 100 combine to meet the requirements of a wide spectrum of individuals. The increased modularity of design of the prosthesis 100 recreates the effortless heel-to-toe action of the natural gait of the wearer. During each step, the prosthesis 100 stores and then releases energy to provide a smooth, even gait without the usual "breaks" or "jerks" characteristic of the prior art constructions incorporating rigid members connected by pivots or the like.

An important aspect of the invention is the infinite spring-fatigue life of the laminated graphitic filamentary construction utilized in the prosthesis 100 which is impervious to water, humidity, heat, cold or corrosion. There are no component parts to malfunction in respect to one another, linkages or connections to fail, no wood or conventional foamed heels to become damaged or deteriorate.

Of great importance is the conformity of the various modular elements of the prosthesis 100 to the needs of the individual wearing the same. By the interaction of the various modular components, delicate nuances of orientation, adjustment and flexibility may be achieved which are totally unattainable by prior art constructions which provide a plurality of interacting components whose linkages are controlled by relatively inflexible relationships. Consequently, the prosthesis 100 is adaptable to active and non-active patients and is suitable for the young, active amputee who will wear it while enjoying the pleasures of running, swimming and other strenuous athletic activities. Conversely, an increasing number of older, somewhat less active patients who wish to achieve the pleasure of a natural, fatigue-free gait are satisfied by the ultralightweight and compliant characteristics of the prosthesis 100.

Significant also is the ease with which the cosmesis can be applied to the prosthesis 199 t achieve substantial identity in appearance with the sound limb of the wearer of said prosthesis. The most important aspect of the prosthesis is the provision of the modular heel which imparts hitherto unobtainable flexibility of movement to the foot portion of the prosthesis and permits life-like movement of the toe to be achieved.

In addition, the optimum length of the shin portion of the pylon is ten inches but lies in a range between eight and a half and ten inches. Moreover, the lower slot 162 in the upper extremity 106 of the pylon 104 can be horizontal to permit lateral adjustment of the pylon 104.

While I have described the various improvements of my invention hereinabove, it will be obvious to those skilled in the art that various substitutions, alterations and modifications thereof may be made without departing from the scope of the claims.

I claim:

1. A lower leg prosthesis comprising: an elongated pylon formed form resin-impregnated, high-strength filament, said pylon having an upper extremity, an intermediate shin portion and a lower forward foot portion formed integrally with one another, said foot portion extending downwardly and forwardly of said shin portion so as to have substantially low energy absorption compliance in response to vertical loads thereon, and a heel portion secure to said forward foot portion and fabricated from said resin-impregnated, high-strength filament, said shin portion of said pylon having a cross section with a high moment of inertia about an axis generally aligned with the fore and aft direction and a relatively low area moment of inertia about a horizontal axis perpendicular to the fore and aft direction, whereby said shin portion and said forward foot portion may flex in a vertical fore an after plane and not in a vertical transverse plane, the upper extremity of said pylon being rigid and of greater cross section than said shin portion to restrict the length of said shin portion and provide for modular fitment of said pylon by being cut and adjusted to an amputee without affecting the compliant response of said shin and foot portions of said pylon.

2. The prosthesis of claim 1 wherein said heel portion of said prosthesis is attached to the underside of said foot portion.

3. The prosthesis of claim 2 wherein said underside attachment of said heel portion to said foot portion provides an intersection space, and a leverage block located in said intersection space to determine the lever arm of said foot portion with respect to the forward portion of said foot and said shin portion of said pylon.

4. The prosthesis of claim 1 wherein the rigidity of said upper extremity of said pylon is imparted thereto by thickening of said upper extremity with respect to the shin portion of said pylon.

5. The prosthesis of claim 4 wherein said thickness of said upper extremity is in a fore and aft direction.

6. The prosthesis of claim 4 in which said rigidity-achieving thickness is in a direction normal to the fore and aft direction.

7. A lower leg prosthesis comprising: an elongated, generally vertically oriented pylon formed from resin-impregnated, high-strength filament, said pylon having an upper, rigid extremity, an intermediate shin portion and a lower forwardly extending foot portion, all of said upper extremity, shin portion and foot portion being formed integrally with one another and having said high-strength filaments extending from said upper extremity into and through said forwardly extending foot portion, and a rearwardly extending heel portion secured to said forwardly extending foot portion, said rearwardly extending heel portion being demountable from said forwardly extending foot portion and being fabricated from resin-impregnated, high-strength filaments.

8. The prosthesis of claim 7 in which the rigidity of said upper extremity of said pylon is achieved by the thickening of said upper extremity through the utilization of additional filamentary and resinous materials.

9. The prosthesis of claim 7 in which said upper extremity is thicker than the adjacent shin portion of said pylon to impart rigidity thereto.

10. The prosthesis of claim 9 in which said rigid upper extremity is of generally rectangular cross section.

11. The prosthesis of claim 7 in which said foot portion is secured to the underside of said forwardly extending foot portion to define an intersection space between said heel portion and said forwardly extending foot portion.

12. The prosthesis of claim 11 in which a leverage determining means is inserted into said intersection space to determine the length of the lever arm of said heel portion.

13. The prosthesis of claim 7 in which said forwardly extending foot portion and heel portion are provided with shock absorption means on the undersides thereof.

14. The prosthesis of claim 7 in which said rigid upper extremity of said pylon may be cut to a length suitable for adaptation to the height of the user of the prosthesis and wherein fastening means are provided to secure said rigid upper extremity to a stump socket.

15. A lower leg prosthesis comprising: a generally vertically oriented pylon fabricated from resin-impregnated, high-strength filamentary materials, said pylon including a rigid upper extremity having a lower end, an intermediate shin portion and a forwardly oriented foot portion, a rearwardly extending heel portion formed from resin-impregnated filamentary material, said heel portion being secured to the underside of said forwardly extending foot portion, the lower end of said upper extremity being vertically positioned no more than ten inches above the supporting surface of said foot and heel portions, wherein the configuration of said upper extremity renders it more rigid than said intermediate shin portion.

16. A lower leg prosthesis comprising: a generally vertically oriented pylon fabricated from resin-impregnated, high-strength filamentary materials, said pylon including an upper extremity, an intermediate shin portion and a forwardly oriented foot portion, a rearwardly extending heel portion formed from: resin-impregnated filamentary material, said heel portion being secured to the underside of said foot portion, said underside and the upper surface of said heel portion adjacent said securement of said heel portion to said foot portion defining a space, and lever arm length-determining means interposed between said foot and heel portions in said space to determine the length of the lever arm of said heel portion.

17. The prosthesis of claim 16 in which said lever arm length-determining means is constitute by an elastomeric member interposed between said foot and heel portions adjacent the point of securement thereof.

18. The prosthesis of claim 16 in which said heel portion is demountably secured to said foot portion to facilitate the affixation of different stiffnesses of heel portions to said foot portion.

* * * * *

UNITED STATES PATENT AND TRADEMARK OFFICE
CERTIFICATE OF CORRECTION

PATENT NO. : 4,822,363
DATED : April 18, 1989
INVENTOR(S) : Van L. Phillips

It is certified that error appears in the above-indentified patent and that said Letters Patent is hereby corrected as shown below:

On the title page, item [63] Related U.S. Application Data" after the word "abandoned", insert --, which is a continuation-in-part of Ser. No. 512, 180, filed Jul. 11, 1993, issued as U.S. Pat. No. 4,547,913--.

Col. 14, line 46 (claim 1), repalce "form" with --from--; line 53, replace "secure" with --secured--; and line 61, replace "an after" with --and aft--.

Col. 16, line 42 (claim 17), repalce "constitute with" --constituted--.

Signed and Sealed this

Twenty-second Day of February, 1994

Attest:

BRUCE LEHMAN

*Attesting Officer*     *Commissioner of Patents and Trademarks*